US007235676B2

(12) United States Patent
Khan et al.

(10) Patent No.: US 7,235,676 B2
(45) Date of Patent: Jun. 26, 2007

(54) CATALYTIC PROCESS FOR THE PREPARATION OF EPOXIDES FROM ALKENES

(75) Inventors: Noor-ul Hasan Khan, Gujarat (IN); Sayed Hasan Razi Abdi, Gujarat (IN); Rukhsana Ilyas Kureshy, Gujarat (IN); Surendra Singh, Gujarat (IN); Irshad Ahmad, Gujarat (IN); Raksh Vir Jasra, Gujarat (IN); Pushpito Kumar Ghosh, Gujarat (IN)

(73) Assignee: Council of Scientific & Industrial Research, New Delhi (IN)

( * ) Notice: Subject to any disclaimer, the term of this patent is extended or adjusted under 35 U.S.C. 154(b) by 193 days.

(21) Appl. No.: 10/823,318

(22) Filed: Apr. 13, 2004

(65) Prior Publication Data

US 2005/0222440 A1 Oct. 6, 2005

Related U.S. Application Data

(60) Provisional application No. 60/558,288, filed on Mar. 31, 2004.

(51) Int. Cl.
C07D 301/12 (2006.01)
(52) U.S. Cl. .................................... 549/531
(58) Field of Classification Search ............... 549/531
See application file for complete search history.

(56) References Cited

U.S. PATENT DOCUMENTS

| 3,053,856 | A | 9/1962 | Payne et al. ............. 260/348.5 |
| 4,410,501 | A | 10/1983 | Taramasso et al. ......... 423/326 |
| 4,701,428 | A | 10/1987 | Bellussi et al. ................ 502/8 |
| 4,833,260 | A | 5/1989 | Neri et al. ................... 549/531 |
| 5,041,569 | A | 8/1991 | Enomoto et al. ............ 549/531 |
| 5,145,968 | A | 9/1992 | Monnier et al. ............. 546/268 |
| 5,155,241 | A | 10/1992 | Nishibe et al. .............. 549/531 |
| 6,583,300 | B1 | 6/2003 | Leyshon et al. ............ 549/529 |

FOREIGN PATENT DOCUMENTS

EP 0540009 A1 5/1993

OTHER PUBLICATIONS

Lane et al, JACS, vo. 124, p. 11946-11954 (2002).*
Daniel Swern; *Electronic Interpretation of the Reaction of Olefins with Organic Per-acids*, The Journal of the Americal Chemical Society, vol. 69, Jul.-Dec. 1947, pp. 1692-1698.

Teruaki Mukaiyama et al.; *Recent Advances in Aerobic Oxygenation*, Bull. Chem. Soc. Jpn., 68., No. 1, (1995), pp. 17-35, 1 Fig. 14 Tables.
Gianluca Pozzi et al.; *Cobalt tetraarylporphyrin-catalysed epoxidation of alkenes by dioxygen and 2-methylpropanol under fluorous biphasic conditions*, Chem. Commun., 1997, pp. 69 and 70.
George B. Payne et al.; *Reactions of Hydrogen Peroxide. VII. Alkali-Catalyzed Epoxidation and Oxidation Using a Nitrile as Co-reactant*, The Journal of Organic Chemistry, vol. 26, No. 3, Mar. 1961, pp. 659-663.
G. B. Payne, *A Simplified Procedure for Epoxidation by Benzonitrile-Hydrogen Peroxide, Selective Oxidation of 2-Allylcyclohexanone*, Tetrahedron, 1962, vol. 18, pp. 763-765.
Benjamin S. Lane et al.; *A Cheap, Catalytic, Scalable, and Environmentally Benign Method for Alkene Epoxidations*, J. Am. Chem. Soc. 2001, 123, pp. 2933 and 293, 1 Fig., 1 Table.
David E. Richardson et al.; *Equilibria, Kinetics and Mechanism in the Bicarbonate Activation of Hydrogen Peroxide: Oxidation of Sulfides by Peroxymonocarbonate*, J. Am. Chem. Soc. 2000, 122, pp. 1729-1739, 8 Figs.
Heather Riley Tetzlaff et al.; *Kinetics and Mechanism of the Epoxidation of Allylic Alcohols by Hydrogen Peroxide with Methyltrioxorheniium as Catalyst*, Inorg. Chem. 1999, 38, pp. 881-885, 1 Table, 3 Figs.
George Majetich et al.; *Carbodiimide-promoted Epoxidation of Olefins with Dilute Aqueous Hydrogen Peroxide*, SYNLETT, Jul. 1996, p. 649-651, 1 Table.
Eric N. Jacobsen; *Transition Metal-catalyzed Oxidations: Asymmetric Epoxidation*, Comprehensive Organometallic Chemistry II, vol. 12, pp. 1097-1135, 20 Figs., 7 Tables.
Alexander McKillop et al.; *Sodium Perborate and Sodium Percarbonate: Cheap, Safe and Versatile Oxidising Agents for Organic Synthesis*, Tetrahedron Report No. 373, 1995, vol. 51, No. 22 pp. 6145-6166, 1 Table.
John O. Edwards; *Nukcleophilic Displacement on Oxygen in Peroxides*, Peroxide Reaction Mechanisms, Conference held at Brown University, Providence, RI, Jun. 15-17, 1960, pp. 67-107, 2 Figs., 10 Tables.
David E. Richardson et al.; *Kinetics and Equilibrium Formation of a Weakly Basic Oxidant System for Decontamination*, ERDEC Scientific Conference, 1999, pp. 293-298, 2 Tables.

* cited by examiner

*Primary Examiner*—Bernard Dentz
(74) *Attorney, Agent, or Firm*—Madan, Mossman & Sriram, P.C.

(57) ABSTRACT

An improved catalytic process for the preparation of epoxides from alkenes using a combination of transition metal salt, an inorganic promoter and an organic additive in absence of solvent or in the presence of a solvent with commercially available hydrogen per oxide has been disclosed. Thus, styrene oxide was prepared at a kilogram scale in 86% isolated yield with purity >95%.

8 Claims, No Drawings

CATALYTIC PROCESS FOR THE PREPARATION OF EPOXIDES FROM ALKENES

CROSS REFERENCE TO RELATED APPLICATIONS

This application claims priority from the U.S. Provisional Patent Application 60/558,288, filed Mar. 31, 2004, the Provisional Application having the same inventorship as the present application.

FIELD OF INVENTION

The present invention relates to an improved catalytic process for the preparation of epoxides from alkenes. More particularly this invention relates to the use of transition metal salt in combination with inorganic base and an organic compound in the presence of hydrogen peroxide from alkene viz. styrene, indene, cyclohexene, 1,2-dihydronaphthalene, isoprene, α-pinene, 1-hexene, 1-octene, t-4-octene. These epoxides find applications as intermediates in the synthesis of perfumery chemicals, drug, pharmaceuticals and agrochemicals.

BACKGROUND OF THE INVENTION

Epoxides are highly reactive chemical compounds which as a result of their reactivity, can be used in a wide variety of application. Epoxidation is a second-order and is highly exothermic reaction with heat of reaction (ca. 250 kJ/mol); therefore, care must be taken at all times to ensure safe operation. Electron-donating groups, e.g., alkyl groups at the double bond carbon atoms, enhance the reaction rate while electron-withdrawing groups have the opposite effect and may sometimes stop the reaction entirely. For example, it has been reported (D. Swern, *J. Am. Chem. Soc.* 69 (1947) 1692) that 2-Butene reacts considerably faster than propene, whereas allyl chloride reacts slower.

The preparation of epoxides by the oxidation of alkenes is a technically important process of economical significance. Preferably epoxides are formed by the reaction of an alkene with an oxidizing agent in the presence of a catalyst. Various oxidizing agents such as commercial bleach, organic hydroperoxides, organic per acids, iodosyl arines, oxones, molecular oxygen (in the form of pure oxygen or atmospheric oxygen) and hydrogen peroxide have been used to prepare a variety of alkene epoxides.

Hydrogen peroxide is a high oxygen content, environmentally friendly oxidant for which water is the sole by-product in heterolytic oxidation, but it is a slow oxidant in absence of activation due to the poor-leaving tendency of the hydroxide ion. (G. Strukul, *Catalytic Oxidation with Hydrogen Peroxide as oxidant*: Kluwer: Dordrecht, 1992 and J. O. Edwards, *In Peroxide Reaction Mechanism*; O. J. Edward, Ed. Interscience: New York, 1962; pp, 67). Transition metal salts or complexes have been used as catalyst for alkene epoxidation with aqueous $H_2O_2$ (E. N. Jacobsen, *In Comprehensive Organometallic Chemistry* II; E. W. Abel, F. G. Stone, E. Wilkinson, Eds. Pergamon: New York, 1995. Vol. 12 p. 1097; H. R. Tetzlaff, J. H. Espenson, *Inorg. Chem.* 38 (1999) 881). Other methods for activation of $H_2O_2$ include forming reactive peroxy acids from carboxylic acids (D. Swern, *In Organic peroxides*; D. Swern Eds. Wiley Interscience, New York 1971 Vol. 2 p. 355) forming peroxycarboximidic acid from acetonitrile (G. B. Payne P. H. Deming, P. H. William, *J. Org. Chem.* 26 (1961) 659) generation of peroxyurea (G. Majetich, R. Hicks, *Synlett.* (1996) 694), or using perborate or sodium percarbonate in strongly basic solution (A. McKillop, W. R. Sanderson, *Terahedron*, 51 (1995) 6145). A method for activating hydrogen peroxide with bicarbonate ion in alcohol/water solvents was described by R. S. Drago et al. in *Proceeding of* 1997 *ERDEC scientific Conference on Chemical and Biological Defense Research* and D. E. Richardson et al. in *Proceeding of* 1998 and *ERDEC scientific Conference on Chemical and Biological Defense Research, ERDEC,* 1999. In the bicarbonate-activated peroxide system, the active oxidant peroxymonocarbonate ion, $HCO_4^-$ is presumably produced via the perhydration of $CO_2$ (D. E. Richardson et al., *J. Am. Chem. Soc.,* 122 (2000) 1729). Peroxymonocarbonate is an anionic peracid and is a potent oxidant in aqueous solution. Similarly nitrites have also been shown to activate hydrogen peroxide via in-situ production of potent epoxidising reagent-peroxyimidic acids in alkaline media (in general known as Payne system; G. B. Payne et al., *J. Org. Chem.* 26 (1961) 659; G. B. Payne, *Tetrahedron* 18 (1962) 763).

Reference may be made to A. Wurtz, in *Ann.,* 110 (1859) 125 which discloses an industrial process for epoxidising double bond via the chlorohydrin, which uses chlorine as the oxidizing agent (in situ generation of commercial bleach). Disadvantages of the process are (i) there is a simultaneous production of calcium chloride as a by-product of the dehydrochlorination of the chlorohydrin, which has low economic value; (ii) this process generates chlorides of sodium and calcium as inorganic effluent in excess (5–6 equivalent more than the product); (iii) the process is not ecofriendly because of the use of chlorine.

D. Swern in "Organic Peroxy Acids as Oxidizing Agent": D. Swern in Epoxidation, *"Organic Peroxides,"* 2, 5, Wiley-Interscience, New York 1971, pp. 355 described epoxidation of long-chain alkenes including vegetable oils (e.g., soya bean oil), polybutadiene, natural and synthetic rubbers and polyesters with in situ formation of performic acid or peracetic acid as oxidant. The major drawbacks in this system are (i) the peracids used are under anhydrous conditions and are in high concentrations. Under these conditions these per acids (especially lower alkyl per acids) are highly explosive; (ii) under aqueous condition, epoxides are readily hydrolyzed unless the medium is appropriately buffered; (iii) the cost of per acid is high thus it adversely affects the economics of the process.

D. W. Leyshon et al. in U.S. Pat. No. 6,583,300 (2003) discloses a process for the production of propene oxide by the reaction of propene with a hydroperoxide in presence of titanium containing molecular sieve as catalyst at 63° C. and 1000 psig pressure wherein reaction effluent comprises by weight 58% propene, 4.6% propene oxide, 10.8% methyl benzyl alcohol, 18.2% ethyl benzene, 8.4% others. The process has the following disadvantages. (i) it produces a low-cost alcohol as a by-product in an amount chemically equivalent to the epoxidised compound formed; ii) selectivity of the process is poor as it lead to the formation of unidentified products to the tune of nearly 18% by weight; iii) the catalyst deactivates after first run and need to regenerated; iv) the method is not suitable for higher and aromatic alkenes.

J. R. Monnier, et al. in U.S. Pat. No. 5,145,968, (1992) has disclosed selective monoepoxidation of styrene and styrene analogs with molecular oxygen (0.01–30 mol along with a diluent gas helium) in the presence of a silver-containing catalyst comprising 2 to 20 weight % silver, 0.01 to 2 weight % of an alkali metal nitrate or chloride as catalyst promoter on alumina support. Epoxidation reaction was conducted at a reaction pressure of 1–30 atmosphere over a temperature range of 100°–325° C., wherein conversions to the product epoxide was in the range of 5–60% with selectivity to styrene oxide was of 50–78 mol %. However, this process has following disadvantages (i) operating temperatures are higher at which alkene and oxygen mixture is a potential explosive; (ii) Conversions and selectivities are moderate which limits its scope for commercial application; (iii) utilizes expensive helium gas as diluent for maintaining oxygen concentration.

T. Mukaiyama in *Bull. Chem. Soc. Jpn.* 68 (1995) 17 and G. Pozzi in *Chem. Commun.* (1997) 69 reported the use of molecular oxygen (in the form of pure oxygen or atmospheric oxygen) as the oxidant for achieving high epoxide yield of epoxycyclohexane, in presence of an aldehyde as additive in methylene chloride as solvent, using iron/copper powder and catalytic amounts of acetic acid as catalyst. In continuation of this study, S-I. Murahashi et al. in EP 0 540 009 (1993) disclosed that a catalyst can even be completely dispensed with under dilute (using excess of methylene chloride) condition. Both of these process have the following disadvantages (i) the process uses large amounts of methylene chloride. as solvent, which is ecologically and toxicologically dangerous; (ii) other solvents such as toluene cannot replace methylene chloride and results in lower yields and side reactions through oxidation of the solvent; (iii) many conventional organic solvents form explosive mixture with molecular oxygen, which greatly limits its application in industry; (iv) in the process of oxidation of the aldehyde additive gets converted into corresponding acid, which is not desirable as far as process economy is concerned.

G. B. Payne et al. in U.S. Pat. No. 3,053,856 disclosed the use of hydrogen peroxide as an oxidizing agent in the presence of a catalyst such as tungstic acid or in the presence of an organic nitrile. But these two methods have drawbacks (i) in the case of tungstic acid the product epoxide is hydrolyzed to the corresponding glycol under the reaction condition; (ii) in the case of organic nitrile an equivalent quantity of the corresponding amide is generated along with the product epoxide; (iii) the amide generated is low cost besides it is required to be separated from the product epoxide by way of distillation process which further adds to the cost of the process, hence industrially undesirable.

M. Taramasso et al. in U.S. Pat. No. 4,410,501, (1983), G. Bellussi et al. in U.S. Pat. No. 4,701,428, (1987) and C. Neri et al. in U.S. Pat. No. 4,833,260, (1989) disclosed that titanium silicalites are effective catalysts for the epoxidation of olefinic compounds with hydrogen peroxide as oxidant in the presence or in the absence of solvents. In these cases the epoxidation is effected in a protic medium such as, an alcohol or water where alcohol is considered as a co-catalyst. However, these processes suffer following disadvantages i) the catalyst requires treatment with a neutralizing agent for suppressing the superficial acid sites of the catalyst, responsible for the formation of these undesired byproducts. In doing so inorganic salts are generated that are environmentally not desirable; ii) the small pore size of the catalyst titanium silicalites (5.6×5.3 Å) limits its application to the smaller alkenes; iii) epoxidation of a wide range of bulkier alkenes cannot be epoxidated with these catalysts since alkenes cannot reach the active sites. S. Enomoto, et al. in U.S. Pat. No. 5,041,569 (1991) and K. Nishibe et al. in U.S. Pat. No. 5,155,241 (1992) have disclosed the preparation of styrene oxide by reacting styrene and hydrogen peroxide in heterogeneous system in the presence of a bis (tri-n-alkyltinoxy)molybdic acid with an amine and an inorganic anion respectively using 60% hydrogen peroxide as a source of oxygen which took 24 hours to give 77–82% yield with 90% epoxide selectivity at 24° C. in presence of a water insoluble solvent like chloroform, dichloroethane, benzene and acetonitrile. The drawbacks of this system are i) it requires chlorinated and other hazardous solvents; ii) the yields and selectivity are on the lower side and takes longer time to achieve such conversions; iii) it requires highly explosive concentration of hydrogen peroxide (60%) to achieve above-mentioned conversions, which is not favorable for its application in industry.

B. S. Lane et al. *J. Am. Chem. Soc.*, 123 (2001) 2933 described a method for activating buffered hydrogen peroxide (10 equivalent) with bicarbonate ion in either alcohol/water or dimethyl formamide/water in 1:1.4 ratio as solvents where active peroxymonocarbonate ion, $HCO_4^-$ is presumably produced via the perhydration of $CO_2$. Using this combination it has been reported to give a conversion of 93% for styrene to styrene oxide in 24 h. The system has following disadvantages i) amount of buffered $H_2O_2$ (10 equivalent) is appreciably large to obtain the high conversions thus oxygen atom efficiency for hydrogen peroxide is poor and require to handle very large volumes making the process not viable at commercial level; ii) it takes extended time period (16 h) to add the buffered $H_2O_2$ as the reaction is highly exothermic under these reaction conditions.

G. Majetich et al. in *Synlett* (1996) 649 have described acidic/base carbodiimide-promoted epoxidation of 3-phenyl 1-propene, cyclic and long chain alkenes, wherein carbodiimide in presence of hyrogen peroxide generates in situ peroxyisourea as the oxidant. The yields were found between 38–71%. This process though attractive suffers following disadvantages (i) the olefin should be soluble in alcoholic solvent, thus limits the scope of the method for other alcohol insoluble alkenes; (ii) the carbodiimde used was dicyclohexylcarbodiimide and is expensive while the equivalent amount of the urea generated at the end of the reaction is of low value; (iii) efficiency of oxygen atom utilization per mole of substrate is very poor and requires large volumes (10 fold excess) of oxidant. Hence, the possibility of scaling up such systems is difficult for industrial applications.

OBJECTIVE OF INVENTION

The main object of the present invention is to provide An improved catalytic process for the preparation of epoxides from alkenes which obviates the drawbacks as detailed above.

Another object of the present invention is to provide an improved process of alkene epoxidation using an inorganic promoter and an organic additive in the absence of an organic solvent or in the presence of a solvent using hydrogen peroxide as oxidant at moderate temperature in 2–7 h.

Yet another object of the present invention is to provide the catalytic activity of the transition metal salt in an organic solvent free reaction condition to obtained epoxide conversion of >99% and epoxide selectivity in the range of 95 to 97%.

Yet another object of the present invention is to provide a catalytic processes using transition metal salt for epoxidation of alkenes under moderate condition of temperature and pressure.

Yet another object of the present invention is to develop a catalytic process for epoxidation of alkene using $H_2O_2$ as an oxidant.

In still another object of the present invention is to achieve epoxide conversion even in absence of transition metal salt.

SUMMERY OF THE INVENTION

The present invention relates to an improved catalytic process for the preparation of epoxides from alkenes. More particularly this invention relates to the use of transition metal salt in combination with inorganic base and an organic compound in the presence of hydrogen peroxide from alkene viz. styrene, indene, cyclohexene, 1,2-dihydronaphthalene, isoprene, α-pinene, 1-hexene, 1-octene, t-4-octene. These epoxides find applications as intermediates in the synthesis of perfumery chemicals, drug, pharmaceuticals and agrochemicals.

DETAILED DESCRIPTION OF THE INVENTION

Accordingly the present invention provides An improved catalytic process for the preparation of epoxides from alkenes which comprises reacting an alkenes in a concentration range of 0.001 mol to 10 mol in presence or in absence of a transition metal salt in a concentration range of 0.01 mmol to 0.01 mol combination with an inorganic base in a concentration range of 0.0003 mol to 4.0 mol and an organic compound in a concentration range 0.02 mol to 30.0 mol as catalyst under biphasic homogeneous system and continuous stirring with hydrogen peroxide as a source of oxygen over a time period 2 to 10 h at a temperature range of −10° to 80° C., the resulting epoxides with a conversion of >99% and 95% selectivity if it is liquid, is separated from aqueous layer of the reaction mixture by layer separation method after 15 h alternatively by solvent extraction method in case of partially water soluble/solid epoxides.

In an embodiment of the present invention, the alkenes used may be selected from styrene, indene, cyclohexene, 1,2-dihydronaphthalene, isoprene, α-pinene, 1-hexene, 1-octene and t-4-octene.

In another embodiment of the present invention, transition metal salt wherein the transition metal may be cobalt, manganese, nickel, copper, iron, chromium and vanadium while the counter ion like chloride, bromide, iodide, carbonate, bi-carbonate, perchlorate, sulphate, nitrate, acetate, phosphate.

In yet another embodiment of the present invention epoxidation reactions may be conducted under biphasic conditions in the absence of an organic solvent or in the presence of a solvent that may be selected from benzene, flurobenzene, chlorobenzene, nitrobenzene, 1,4-dioxane acetonitrile, benzonitrile, formamide, acetamide, propamide, dimethylformamide, dimethylacetamide, dichloromethane and dichloroethane in combination of water.

In another embodiment of the present invention the inorganic promoter may be carbonates and bicarbonates of alkali metals like lithium, sodium, potassium and cesium. In yet another embodiment of the present invention an organic additive may be nitriles e.g. acetonitrile and benzonitrile, amides e.g. formamide, acetamide, propamide, dimethylformamide, dimethylacetamide, urea, alkyl substituted urea, aryl substituted urea and thio-urea.

According to the present invention, the catalytic oxidation of alkenes proceeds through the following equation

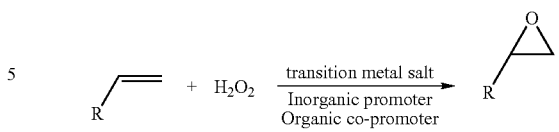

The reaction was conducted on laboratory scale in 250 ml two-necked round bottom flask fitted with an efficient water condenser. Laboratory reagent grade alkenes were used as a substrate. The catalytic conversion was carried out in presence of inorganic salts and organic co-promoter. Highly active per oxo intermediate species, was generated in situ by slow addition of hydrogen peroxide required for epoxidation. The reaction mixture was allowed to age at 20° C. with constant stirring to yield the respective epoxides.

The process according to the present invention was carried out by using alkene concentration in the range of 0.007 to 15 mol, preferably in the range of 0.01 to 10 mol by catalytic conversion using $H_2O_2$ as oxidant at a moderate temperature and atmospheric pressure. The epoxidation reaction was carried out in combination with inorganic and organic promoters under biphasic homogeneous system. Higher yields of alkene epoxides were obtained when the alkene concentration was more than 0.1 mol in combination with (i) inorganic promoter in the range of 0.0003 mol to 4 mol and (ii) organic co-promoter in the range of 0.02 mol to 30 mol. The product, alkene oxide was extracted, distilled and characterised by GLC and $^1$H NMR.

In the preferred invention, the temperature of the reaction mixture may be maintained in the temperature range of −10 to 110° C., preferably in the range of −5 to 75° C. The catalytic reaction proceeds through the catalytic oxidation at normal to boiling temperature of solvents used and atmospheric pressure. At temperature below −5° C. the catalytic conversion is very slow and the respective oxides obtained after 6 h was only 40%. Gradual increase of the temperature to ca 70° C. helps in achieving the complete conversion of alkenes to their respective epoxides.

In accordance with the present invention, the transition metal salt plays a very vital role in activating the alkenes. The metal salts may be added to the reaction mixture in the concentration range of 0.007 mol to 0.02 mol, preferably in the range of 0.01 mmol to 0.01 mol. With low quantity metal salts (<0.007 mmol) the catalytic reaction is sluggish and the conversion obtained is less than 10%. The use of optimal quantity of metal salts is essential as it definitely catalyses the transformation, but at the same it tends to decompose hydrogen per oxide. This may result in lower yield of epoxides and need of higher quantities of hydrogen peroxide.

In carrying out the present invention, the time required for the addition of hydrogen peroxide followed by aging of the reaction are critical in achieving higher yields and conversion. The time of addition may be varied in the range of 1 to 10 h, preferably in the range of 2 to 6 h followed by aging in the range of 2 to 20 h preferably in the range of 3 to 15 h. It was observed that decreasing the time of addition below 1 h followed by aging less than 2 h resulted in lower conversion of alkene to epoxide. No advantage has occurred by increasing the time of addition and subsequent aging period beyond 6 h and 15 h respectively.

In the present invention it was observed that the concentration of oxidant may be varied in the range of 5 to 55%, preferably in the range of 10 to 50% for obtaining higher oxygen atom efficiency with respect to the substrate (alkenes). Moreover, along with hydrogen peroxide the optimum quantity metal salt is essential, as the later also tends to decompose hydrogen peroxide. This may result in the need of higher quantity of hydrogen peroxide, which may adversely effect the economics of the process. A combination of metal salts with hydrogen peroxide forms a highly active peroxo intermediate species, which enhances the conversion of alkenes to epoxides.

The present invention relates to the preparation of alkene oxides suitable for various applications. These alkene oxides were prepared from a wide range of alkenes by catalytic conversion using hydrogen peroxide as oxidant at moderate temperature and atmospheric pressure. The epoxidation reaction was affected by the use of transition metal salts as catalyst in combination with inorganic base and an organic solvent wherein the conversion and selectivity were of the order higher than that reported in literature. The method of present invention does not require any special device and the use of hazardous and corrosive chlorine gas is dispensed. In the present invention the catalytic process for the preparation of epoxides from alkene in presence and absence of organic solvents and at moderate temperature, yield oxide having high purity. The inventive steps adopted in the presence invention are (i) commercial hydrogen peroxide is used as oxidant for the epoxidation of alkenes and the use of chlorine gas as oxidant is dispensed; (ii) the epoxidation reaction is carried out at lower temperature and atmospheric pressure and does not require higher temperature and pressure; (iii) the epoxidation reaction obviates the need of anhydrous condition and the catalytic conversion takes place in organic and/or aqueous medium; (iv) for most alkenes organic solvent is not needed for the epoxidation reaction to occur, thus makes the process eco-benign, however where ever solvent is required, the same does not form explosive mixture with molecular oxygen (v) the epoxidation reaction is affected using inexpensive transition metal salt as catalyst and the need for expensive tungstic acid, complexes of molybdic acid and silver containing catalyst is dispensed.

In a typical catalytic run, the appropriate transition metal salt, alkene, inorganic salt and organic additive in water was taken in a reaction vessel at a required temperature. The oxidant was added at a defined rate and after completion of reaction epoxide was separated in a separating funnel and purified by distillation or crystallization as the case may be. The purity of the product was determined by Gas Chromatography and $^1$HNMR. The following examples are given by way of illustration of the present invention and therefore should not be construed to limit the scope of the present invention.

EXAMPLE 1

To a mechanically stirred solution of styrene (0.1 mol), dodecane (0.01 mol), urea (2.08 mol), sodium bicarbonate (0.03 mol) and manganese sulphate (0.0001 mol) in 50.0 ml of water at 20° C. is added 30% aqueous hydrogen peroxide (0.22 mol) drop-wise over a period of 4 h. After 4.5 h the organic layer of the reaction mixture was separated by a separating funnel. The aqueous layer was extracted with 4×20 mL diethyl ether. The combined organic layer was distilled to yield styrene oxide. The conversion to epoxide is 99% with 94% selectivity.

EXAMPLE 2

To a mechanically stirred solution of styrene (0.1 mol), dodecane (0.01 mol), urea (2.08 mol), sodium bicarbonate (0.03 mol) in 50.0 ml of water at 20° C. is added 30% aqueous hydrogen peroxide (0.22 mol) drop-wise over a period of 5 h. After 5 h the organic layer of the reaction mixture was separated by a separating funnel. The aqueous layer was extracted with 4×20 mL diethyl ether. The combined organic layer was distilled to yield styrene oxide. The conversion to epoxide is 99% with selectivity 95%.

EXAMPLE 3

To a mechanically stirred solution of styrene (1.0 mol), dodecane (0.1 mol) urea (20.8 mol), sodium bicarbonate (0.3 mol) and manganese sulphate (0.001 mol) in 500 ml of water at 20° C. is added 50% aqueous hydrogen peroxide (2.2 mol) drop-wise over a period of 5 h. After 5 h a separating funnel separated the organic layer of the reaction mixture. The aqueous layer was extracted with 4×20 mL diethyl ether. The combined organic layer was distilled to yield styrene oxide. The conversion to epoxide is 99% with selectivity 94%.

EXAMPLE 4

To a mechanically stirred solution of styrene (1.0 mol), urea (40.8 mol), sodium bicarbonate (0.6 mol) and manganese sulphate (0.001 mol) in 500 ml of water at 0° C. is added 50% aqueous hydrogen peroxide (2.2 mol) drop-wise over a period of 3 hours. The reaction was allowed to stir for 10 hours. After 10 hours a separating funnel separated the organic layer of the reaction mixture. The aqueous layer was extracted with 4×20 mL diethyl ether. The combined organic layer was distilled to yield styrene oxide. The conversion to epoxide is 99% with selectivity 92%.

EXAMPLE 5

To a mechanically stirred solution of styrene (1.0 mol), dodecane (0.1 mol), urea (20.8 mol), sodium bicarbonate (0.3 mol) and manganese sulphate (0.001 mol) in 500 ml of water at 40° C. is added 50% aqueous hydrogen peroxide (2.2 mol) drop-wise over a period of 4 hours. The reaction was allowed to stir for 8 hours. After 8 hours a separating funnel separated the organic layer of the reaction mixture. The aqueous layer was extracted with 4×20 mL diethyl ether. The combined organic layer was distilled to yield styrene oxide. The conversion to epoxide is 99% with selectivity 94%.

EXAMPLE 6

To a mechanically stirred solution of commercial grade styrene (10.0 mol), commercial grade urea (26.6 mol), laboratory grade sodium bicarbonate (3.7 mol) and manganese sulphate (0.01 mol) in 2.50 L of water at 15° C. is added commercial grade 50% aqueous hydrogen peroxide (22.0 mol) slowly over a period of 5 hours. After 5.5 hours a separating funnel separated the organic layer of the reaction mixture. The crude styrene oxide was distilled to yield styrene oxide. The conversion to epoxide is 99% with selectivity 95%.

EXAMPLE 7

To a mechanically stirred solution of indene (0.01 mol), dodecane (0.001 mol), urea (0.208 mol), sodium bicarbonate (0.003 mol) and manganese sulphate (0.1 mmol) in 10.0 ml of water at 20° C. is added 30% aqueous hydrogen peroxide (0.4 mol) in three equal portions over a period of 3 hours.

After 10 hours the reaction mixture was extracted with 4×5 ml diethyl ether. The combined organic layer was dried over anhydrous sodium sulphate. Removal of solvent yielded indene oxide in >99% yield with selectivity 95%.

EXAMPLE 8

To a mechanically stirred solution of cyclohexene (0.01 mol), dodecane (0.001 mol), urea (0.208 mol), sodium bicarbonate (0.003 mol) and manganese sulphate (0.1 mmol) in 10.0 ml of water at 25° C. is added 30% aqueous hydrogen peroxide (0.4 mol) in three equal portions over a period of 3 hours. After 8 hours the reaction mixture was extracted with 4×5 ml diethyl ether. The combined organic layer was dried over anhydrous sodium sulphate. Removal of solvent yielded cyclohexene oxide in 96% yield with selectivity 91%.

EXAMPLE 9

To a mechanically stirred solution of α-pinene (0.01 mol), dodecane (0.001 mol), urea (0.208 mol), sodium bicarbonate (0.003 mol) and manganese sulphate (0.1 mmol) in 10.0 ml of water and 30 ml acetonitrile at 25° C. is added 30% aqueous hydrogen peroxide (0.4 mol) in three equal portions over a period of 3 hours. After 6 hours the reaction mixture was extracted with 4×5 ml diethyl ether. The combined organic layer was dried over anhydrous sodium sulphate. Removal of solvent yielded α-pinene oxide in 85% yield with selectivity 93%.

EXAMPLE 10

To a mechanically stirred solution of 1,2-dihydronaphthalene (0.01 mol), dodecane (0.00 mol), urea (0.208 mol), sodium bicarbonate (0.003 mol) and manganese sulphate (0.1 mmol) in 10.0 ml of water and 30 ml of dichloromethane at 25° C. is added 30% aqueous hydrogen peroxide (0.4 mol) in three equal portions over a period of 3 hours. After 4 hours the reaction mixture was extracted with 4×5 ml diethyl ether. The combined organic layer was dried over anhydrous sodium sulphate. Removal of solvent yielded 1,2-dihydronaphthalene oxide in 99% yield with selectivity 95%.

EXAMPLE 11

To a mechanically stirred solution of styrene (0.01 mol), dodecane (0.001 mol), urea (0.208 mol), sodium bicarbonate (0.003 mol) and cobalt (II) acetate (0.2 mmol) in 10.0 ml of water and 30 ml of dichloromethane at 25° C. is added 30% aqueous hydrogen peroxide (0.5 mol) in three equal portions over a period of 4 hours. After 14 hours the reaction mixture was extracted with 4×5 ml diethyl ether. The combined organic layer was dried over anhydrous sodium sulphate. Removal of solvent yielded styrene oxide in 56% yield with selectivity 80%.

EXAMPLE 12

To a mechanically stirred solution of styrene (0.01 mol), dodecane (0.001 mol), dimethylformamide (0.208 mol), sodium bicarbonate (0.003 mol) and manganese (II) acetate (0.15 mmol) in 10.0 ml of water at 30° C. is added 30% aqueous hydrogen peroxide (0.45mol) in three equal portions over a period of 3 hours. After 8 hours the reaction mixture was extracted with 4×5 ml diethyl ether. The combined organic layer was dried over anhydrous sodium sulphate. Removal of solvent yielded styrene oxide in 56% yield with selectivity 80%.

EXAMPLE 13

To a mechanically stirred solution of styrene (0.01 mol), dodecane (0.001 mol), urea (0.208 mol), sodium bicarbonate (0.003 mol) and nickel (II) acetate (0.15 mmol) in 10.0 ml of water at 30° C. is added 30% aqueous hydrogen peroxide (0.45 mol) in three equal portions over a period of 3 hours. After 8 hours the reaction mixture was extracted with 4×5 ml diethyl ether. The combined organic layer was dried over anhydrous sodium sulphate. Removal of solvent yielded styrene oxide in 45% yield with selectivity 68%.

EXAMPLE 14

To a mechanically stirred solution of styrene (0.01 mol), dodecane (0.001 mol), urea (0.208 mol), sodium carbonate (0.004 mol) and manganese (II) acetate (0.2 mmol) in 10.0 ml of water at 30° C. is added 30% aqueous hydrogen peroxide (0.45 mol) in three equal portions over a period of 3 hours. After 8 hours the reaction mixture was extracted with 4×5 ml diethyl ether. The combined organic layer was dried over anhydrous sodium sulphate. Removal of solvent yielded styrene oxide in 87% yield with selectivity 82%.

EXAMPLE 15

To a mechanically stirred solution of styrene (0.01 mol), dodecane (0.001 mol), urea (0.208 mol), potassium bicarbonate (0.003 mol) and manganese sulphate (0.1 mmol) in 10.0 ml of water at 30° C. is added 30% aqueous hydrogen peroxide (0.5 mol) in three equal portions over a period of 4 hours. After 5 hours the reaction mixture was extracted with 4×5 ml diethyl ether. The combined organic layer was dried over anhydrous sodium sulphate. Removal of solvent yielded styrene oxide in 90% yield with selectivity 90%.

EXAMPLE 16

The same procedure as exemplified in example 1 was repeated with various alkenes viz., isoprene, 1-octene, t-4-octene and chromene except that here the epoxidation reaction was conducted in presence acetonitrile as an organic solvent in combination with water in 3:2 v/v ratio. The results are summarized in Table 1.

TABLE 1

| Alkene | Time (hrs) | % conversion* |
|---|---|---|
| isoprene | 20 | 95 |
| 1-octene | 8 | 26 |
| t-4-octene | 8 | 23 |
| Chromene | 20 | 99 |

*Determined by Gas Chromatography (GC)

The main advantages of the present invention are:
1. Good isolated yields of epoxides are achievable with inexpensive reagents under mild reaction conditions.
2. Organic ligand based metal complexes are not required for the activation of hydrogen peroxide and alkenes under the reaction conditions used in the present invention.

3. Only smaller quantity of commercial LR grade transition metal salt is required to carry the reaction to completion at 1 Kg scale.
4. Under certain reaction conditions the epoxidation reaction of alkene gave high conversion and selectivity even in absence of a transition metal salt.
5. Inorganic salts and organic compounds used to activate hydrogen peroxide are inexpensive and of commercial grade.
6. Under the defined reaction conditions the organic solvent is not required for most of the liquid alkenes.
7. Epoxidation reactions are run in air (no prior oxygen free conditions are required).
8. Final work up protocol at higher scale (at 1 Kg scale) does not require solvent extraction as water insoluble epoxides form a separate layer and thus can be physically separated.
9. Using the present invention high level of conversion and selectivity was achieved within reasonable time period that makes the process viable for industrial application.
10. Reaction rates are significantly faster than reported so far with these alkenes using hydrogen peroxide as oxidant.

We claim:

1. An improved catalytic process for the preparation of epoxides from alkenes, said process comprising the steps of:
  a. reacting, as a reaction mixture including an organic solvent, water, or a combination thereof, an alkene in a concentration range of 0.001 mol to 10 mol in the presence of a transition metal salt in a concentration range of from 0.01 mmol to 0.01 mol, in combination with an inorganic base in a concentration range of 0.0003 mol to 4.0 mol and an organic additive selected from the group consisting of urea, alkyl substituted urea, aryl substituted urea and thio-urea in a concentration range 0.02 mol to 30.0 mol, as catalysts, in a biphasic homogeneous system while continuously stirring with hydrogen peroxide as a source of oxygen over a time period of from 2 to 10 hours at a temperature ranging from −10° to 80° C. to form an epoxide and water, wherein the conversion of the alkene is >99% with at least about 95% selectivity, and
  b. separating the epoxide from the water by a layer separation method or by a solvent extraction method.

2. An improved catalytic process as claimed in claim 1, wherein the alkene is selected from the group consisting of styrene, indene, cyclohexene, 1,2 hydronaphthalene, isoprene, α-pinene, 1-hexene, 1-octene and t-4-octene.

3. An improved catalytic process as claimed in claim 1, wherein the transition metal salt includes a transition metal selected from the group consisting of cobalt, manganese, nickel, copper, iron, chromium and vanadium, and the counter ion is selected from the group consisting of chloride, bromide, iodide, carbonate, bi-carbonate, perchlorate, sulphate, nitrate, acetate, and phosphate.

4. An improved catalytic process as claimed in claim 1, wherein a combination of the organic solvent and water is used, the organic solvent being selected from the group consisting of benzene, fluorobenzene, chlorobenzene, nitrobenzene, 1,4-dioxane acetonitrile, benzonitrile, formamide, acetamide, propamide, dimethylformamide, dimethylacetamide, dichloromethane and dichloroethane, and wherein the organic solvent and water are proportioned 2:3 v/v.

5. An improved catalytic process as claimed in claim 1, wherein the inorganic base is selected from the group consisting of carbonates and bicarbonates of alkali metals.

6. An improved catalytic process as claimed in claim 1, wherein the hydrogen peroxide was maintained at a concentration in the range of 5% to 55%.

7. An improved catalytic process as claimed in claim 1, wherein the reaction mixture is allowed to age for a time period in the range of from 3 to 15 hours prior to separating the epoxide from the water.

8. The improved catalytic process as claimed in claim 5, wherein the alkali metal is selected from the group consisting of lithium, sodium, potassium and cesium.

* * * * *